(12) United States Patent
Takagi (10) Patent No.: US 9,416,418 B2
(45) Date of Patent: Aug. 16, 2016

(54) BIOCHIP AND TARGET DNA QUANTITATIVE METHOD

(71) Applicant: Seiko Epson Corporation, Tokyo (JP)

(72) Inventor: Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/513,788

(22) Filed: Oct. 14, 2014

(65) Prior Publication Data

US 2015/0031587 A1 Jan. 29, 2015

Related U.S. Application Data

(63) Continuation of application No. 12/854,935, filed on Aug. 12, 2010, now Pat. No. 8,889,405.

(30) Foreign Application Priority Data

Sep. 16, 2009 (JP) ................. 2009-214712

(51) Int. Cl.
*C12P 19/34* (2006.01)
*C12Q 1/68* (2006.01)
(Continued)

(52) U.S. Cl.
CPC ............ *C12Q 1/6876* (2013.01); *B01L 3/5025* (2013.01); *B01L 3/50273* (2013.01); *B01L 7/52* (2013.01); *C12Q 1/6851* (2013.01); *B01J 2219/00317* (2013.01); *B01J 2219/00421* (2013.01); *B01J 2219/00529* (2013.01); *B01J 2219/00576* (2013.01); *B01J 2219/00608* (2013.01); *B01J 2219/00693* (2013.01); *B01J 2219/00702* (2013.01); *B01J 2219/00722* (2013.01); *B01L 3/50851* (2013.01); *B01L 3/502738* (2013.01); *B01L 2200/0673* (2013.01); *B01L 2300/087* (2013.01); *B01L 2300/0864* (2013.01); *B01L 2300/0867* (2013.01); *B01L 2300/161* (2013.01); *B01L 2400/0409* (2013.01); *G06F 19/18* (2013.01)

(58) Field of Classification Search
USPC ........................................... 435/287.2, 288.5
See application file for complete search history.

(56) References Cited

U.S. PATENT DOCUMENTS 5,712,125 A    1/1998   Uhlen
6,086,740 A    7/2000   Kennedy
(Continued)

FOREIGN PATENT DOCUMENTS

JP    3138471 U      2/2001
JP    2001-515734 A  9/2001
(Continued)

*Primary Examiner* — Kenneth Horlick
(74) *Attorney, Agent, or Firm* — Harness, Dickey & Pierce, P.L.C.

(57) ABSTRACT

A biochip used for quantitative analysis of a target DNA contained in a sample. The biochip includes a type I chamber that includes a primer designed to bind to the target DNA, an internal standard DNA of a first amount that has a sequence different from a sequence of the target DNA, and is amplifiable with the primer, and a fluorescent probe that is designed to bind to a part of a PCR product of the target DNA and to a part of a PCR product of the internal standard DNA. The fluorescent probe fluoresces differently for the PCR product of the target DNA and the PCR product of the internal standard DNA. The biochip also includes a type II chamber that includes the internal standard DNA of a second amount, the primer, and the fluorescent probe. The first and second amounts are different.

3 Claims, 7 Drawing Sheets

(51) Int. Cl.
   *B01L 3/00*   (2006.01)
   *B01L 7/00*   (2006.01)
   *G06F 19/18*   (2011.01)

(56) References Cited

U.S. PATENT DOCUMENTS

| | | |
|---|---|---|
| 6,623,860 B2 | 9/2003 | Hu et al. |
| 6,648,015 B1 | 11/2003 | Chow |
| 6,857,449 B1 | 2/2005 | Chow |
| 7,351,380 B2 | 4/2008 | Simmons et al. |
| 8,592,160 B2 | 11/2013 | Saito et al. |
| 2002/0028452 A1 | 3/2002 | Wittwer et al. |
| 2005/0026277 A1 | 2/2005 | Festoc |
| 2007/0128608 A1 | 6/2007 | Nakamura et al. |
| 2008/0176290 A1 | 7/2008 | Joseph et al. |
| 2009/0035847 A1 | 2/2009 | Cho et al. |
| 2011/0244522 A1 | 10/2011 | Seo et al. |

FOREIGN PATENT DOCUMENTS

| | | |
|---|---|---|
| JP | 3594598 B2 | 12/2004 |
| JP | 2006-006212 A | 1/2006 |
| JP | 2009-047643 A | 3/2009 |
| WO | WO-92-01812 A1 | 2/1992 |
| WO | WO-95-02067 A1 | 1/1995 |
| WO | WO-99/13113 A1 | 3/1999 |
| WO | WO-2005-059548 A1 | 6/2005 |
| WO | WO-2009-059430 A1 | 5/2009 |

TARGET NUCLEIC ACID SEQUENCE

5' - TTTTCTTCGA　CATTCCGTAG　GAATTTAGAG
　　 GCTTACCACG　CAAGCTAAAC　AC<u>GGCTTGGG</u>
　　 <u>TATTTACATC　ACGAG</u>ATTTT　GTGATAGAAC
　　 CCGAAGCCGA　ATCTCCCT-3'

COMPETING NUCLEIC ACID SEQUENCE

5' - TTTTCTTCGA　CATTCCGTAG　GAATTTAGAG
　　 GCTTACCAGC　CAAGCTAAAC　AC<u>GGCTTGGG</u>
　　 <u>TATTTACATC　ACGAG</u>GGGT　GTGATAGAAC
　　 CCGAAGCCGA　ATCTCCCT-3'

FIG. 6

FORWARD PRIMER SEQUENCE
5' - AGGGAGATTCGGCTTCG-3'

REVERSE PRIMER SEQUENCE
5' - TTTTCTTCGACATTCCGTAGG-3'

FIG. 7

5' - TCTCGTGATGTAAATACCCAAGCC-3'

BIOCHIP AND TARGET DNA QUANTITATIVE METHOD

CROSS-REFERENCE TO RELATED APPLICATIONS

This is a continuation patent application of U.S. application Ser. No. 12/854,935 filed Aug. 12, 2010 (now U.S. Pat. No. 8,889,405), which claims priority to Japanese Patent Application No. 2009-214712, filed on Sep. 16, 2009, all of which are incorporated by reference in their entireties.

BACKGROUND

1. Technical Field

The present invention relates to biochips and target DNA quantitative methods used for quantitative analysis of target DNAs.

2. Related Art

Methods of chemical analysis, chemical synthesis, and other procedures including various analyses in bio-related fields using a microfluidic chip that includes microchannels in a glass substrate or the like have gained attention. The microfluidic chip also has other names, such as a micro total analytical system (micro TAS) and a lab-on-a-chip. Because of advantages such as smaller amounts of samples and reagents, shorter reaction time, and less waste over common analyzing devices, the microfluidic chip is expected to have a wide range of applications, including medical diagnoses, on-site analyses of environment and food, and production of drugs and chemicals. Because the microfluidic chip requires small amounts of reagents, the amounts of expensive reagents can be reduced, and thus the cost of tests can be reduced. Requiring small amounts of samples and reagents means a shorter reaction time and improved test efficiency. Because samples such as blood are used in small amounts, the use of the microfluidic chip for medical diagnoses advantageously reduces the burden on patients.

The PCR (Polymerase Chain Reaction) method is well known as the method of amplifying nucleic acids, including DNA and RNA. In the PCR method, a mixture of target DNA and reagents is put into a tube, and a reaction is allowed in several minutes of repeated cycles at three different temperatures, for example, 55° C., 72° C., and 94° C., using a temperature control device called a thermal cycler. The enzyme (DNA polymerase) acts only on the target DNA and amplifies it about two-fold in each temperature cycle.

Real-time PCR, a technique that uses specific fluorescent probes to quantity DNA as it is amplified, has been put to practical applications. Because of high measurement sensitivity and reliability, real-time PCR has been widely used in research and clinical tests.

In real-time PCR, however, the amplification inhibitors present in a sample may lower the reliability of the results.

Simultaneous measurements of large numbers of reaction systems are usually difficult, because the amounts of DNA extracted from a sample are generally small, and the reagents used for the PCR are usually expensive. The amount of reaction mixture required for PCR is typically several ten microliters, and basically only a single gene can be assayed per reaction system.

WO/2005/059548 describes a method for assaying nucleic acids with the use of a fluorescent probe that hybridizes with both the target DNA and an internal standard DNA. Because this method coamplifies the target DNA and the internal standard DNA, the influence of amplification inhibitors is small, and an expensive, dedicated real-time PCR apparatus is not necessary. However, the method greatly suffers from poor quantification accuracy, particularly when there is a large concentration difference between the target DNA and the internal standard DNA, and the quantifiable concentration range of the target DNA is small.

SUMMARY

An advantage of some aspects of the invention is to provide a biochip and a target DNA quantitative method with which the target DNA contained in a biological sample can be quantified under the small influence of amplification inhibitors contained in the sample, and which allow for a nucleic acid amplification reaction and the quantification of the target DNA with ease over a wide concentration range of the target DNA.

To achieve the above stated advantage, the present invention provides a biochip used for quantitative analysis of a target DNA contained in a sample. The biochip comprises: a type I chamber includes; a primer that is designed to bind to the target DNA; a internal standard DNA of a first amount that has a sequence different from a sequence of the target DNA, and is amplifiable with the primer; and a fluorescent probe that is designed to bind to a part of a PCR product of the target DNA and to a part of a PCR product of the internal standard DNA, and fluoresces differently for the PCR product of the target DNA and the PCR product of the internal standard DNA, and a type II chamber includes; the internal standard DNA of a second amount different from the first amount; and the primer; and the fluorescent probe.

The biochip may further comprise; a first path connected to the type I chamber and the type II chamber; and a reservoir connected to the first path.

The biochip may further comprise; a first group of chambers includes; the type I chamber and the type II chamber that include a first primer used to amplify a first target DNA, and a second group of chambers includes; the type I chamber and the type II chamber that include a second primer different from the first primer and used to amplify a second target DNA different from the first target DNA.

The present invention also provides a quantitative method for a target DNA contained in a biological sample using a biochip. This method comprises: introducing a sample into a type I chamber and a type II chamber of the biochip; the type I chamber includes; a primer that is designed to bind to the target DNA; a internal standard DNA of a first amount that has a sequence different from a sequence of the target DNA, and is amplifiable with the primer; and a fluorescent probe that is designed to bind to a part of a PCR product of the target DNA and to a part of a PCR product of the internal standard DNA, and fluoresces differently for the PCR product of the target DNA and the PCR product of the internal standard DNA, and the type II chamber includes; the internal standard DNA of a second amount different from the first amount; the primer; and the fluorescent probe, performing a PCR amplification in the type I chamber and the type II chamber; measuring a fluorescence intensity of the fluorescent probe in the type I chamber and the type II chamber; determining a regression curve of equation (1) below based on the measured fluorescence intensities in the type I chamber and the type II chamber, and amounts of the internal standard DNA contained in the type I chamber and the type II chamber, $$F = a/(C+b) + c \qquad (1)$$

where F is the fluorescence intensity, C is an amount of internal standard DNA, b is an amount of target DNA contained in the sample, and a and c are predetermined values;

and estimating the amount of the target DNA contained in the sample based on the regression curve.

In the biological sample quantification method, the regression curve may be determined based on a relationship between a ratio of fluorescence intensities measured before and after the PCR amplification reaction and the amount of the internal standard DNA used in the type I chamber and the type II chamber.

In the biological sample quantification method, the regression curve may be determined based on a relationship between the ratio of a fluorescence intensity measured in a first state in which the fluorescent probe binds to a part of the PCR product after the PCR amplification, and a fluorescence intensity measured in a second state in which the fluorescent probe dissociates from the PCR product after the PCR amplification and the amount of the internal standard DNA used in the type I chamber and the type II chamber.

In the biochip, the type I chamber and the type II chamber include known amounts of internal standard DNA, a primer, and a fluorescent probe. The primer is designed to bind to the target DNA. The internal standard DNA has a sequence different from a sequence of the target DNA, and is amplifiable with the primer. The fluorescent probe is designed to bind to a part of a PCR product of the target DNA and to a part of a PCR product of the internal standard DNA. The fluorescent probe fluoresces differently upon binding to the PCR product of the target DNA and upon binding to the PCR product of the internal standard DNA. Because a PCR amplification is performed in the type I chamber and the type II chamber that contain different amounts of internal standard DNA in each other, a user is able to easily perform a PCR amplification and the quantification of the target DNA simply by introducing a sample into the type I chamber and the type II chamber. The quantification of the target DNA using the biochip can be performed under the small influence of the amplification inhibitors that may be present in the sample, and over a wide quantifiable range of the target DNA. Because the introduction of a sample into the biochip is all that is required, a user does not need to go through laborious procedures. Because only small amounts of reagents are used, the biochip enables quantification of the target DNA at low cost and with high accuracy.

The biological sample quantification method is a method for quantifying the target DNA contained in a sample using the biochip. The method includes determining a regression curve of equation (1) above based on the measured fluorescence intensity in the type I chamber and the type II chamber, and the amount of internal standard DNA in the type I chamber and the type II chamber, and estimating the amount of the target DNA contained in the sample based on the regression curve. Thus, the DNA amplification is performed under the small influence of the amplification inhibitors that may be present in the sample, and over a wide quantifiable range of the target DNA. Because the introduction of a sample into the biochip is all that is required, a user does not need to go through laborious procedures. Because only small amounts of reagents are used, the quantification of the target DNA can be performed at low cost and high accuracy.

DESCRIPTION OF EXEMPLARY EMBODIMENTS

Preferred embodiments of the present invention will be described below with reference to the drawings.

1. Embodiment 1.1. Biochip

Figure 1A:
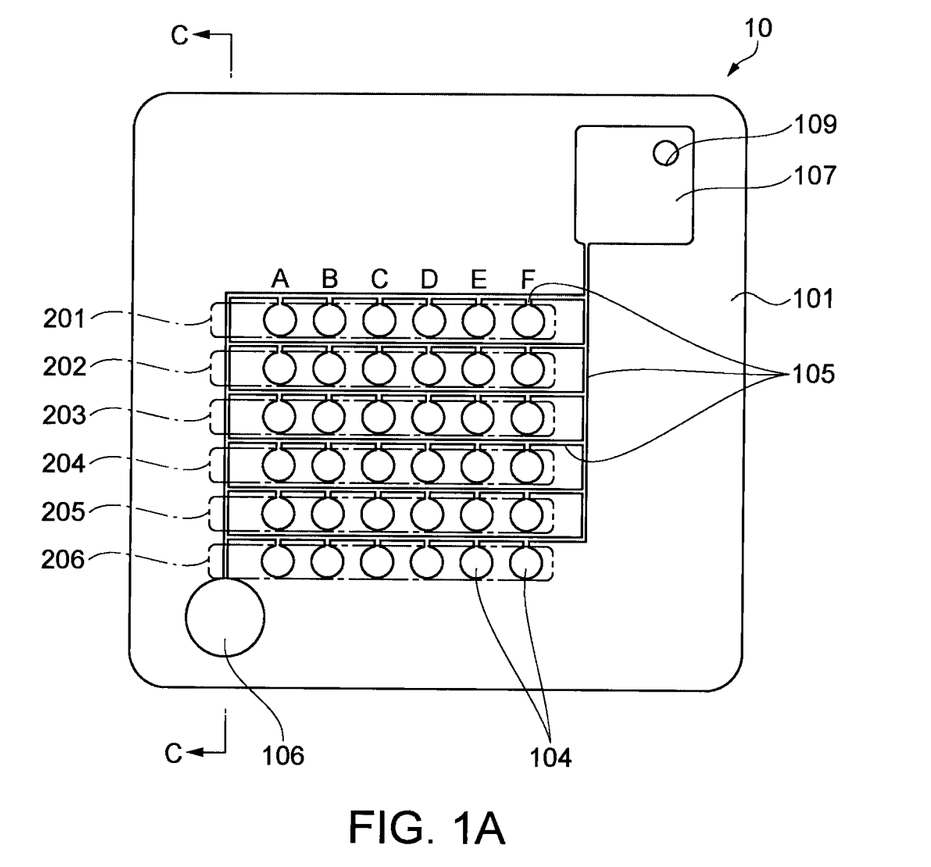
FIG. 1A is a plan view schematically illustrating a configuration of a microchamber array according to an embodiment of the invention.
Figure 1B:
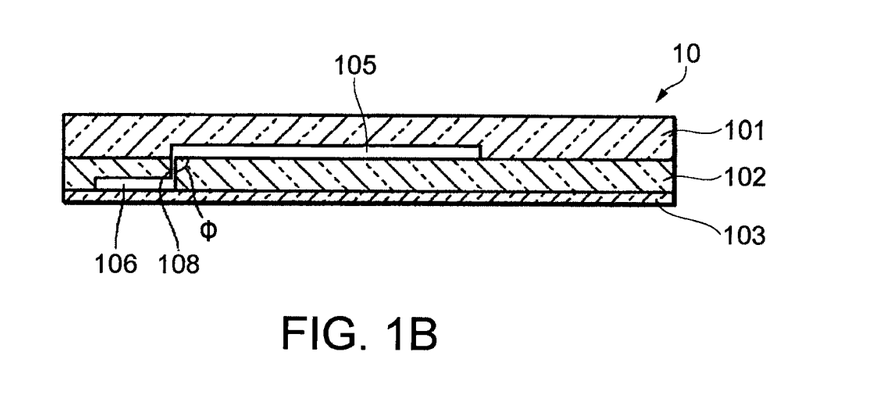
FIG. 1B is a cross sectional view at C-C of FIG. 1A.

FIG. 1A is a plan view schematically illustrating a configuration of a microchamber array (biochip) 10 according to an embodiment of the invention. FIG. 1B is a cross sectional view at C-C of FIG. 1A.

The microchamber array 10 is a biochip (biological sample quantification chip) used to quantify the target DNA contained in a sample. As illustrated in FIG. 1A and FIG. 1B, the microchamber array 10 includes groups of chambers 201, 202, 203, 204, 205, and 206 that contain a plurality of chambers 104. The microchamber array 10 also includes first paths 105 connected to each chamber 104. A reservoir 107 and a waste storage 106 connected to the first paths 105 are also provided. The waste storage 106 is connected to the reservoir 107 via the first paths 105. The microchamber array 10 further includes second paths 108 that connect the first paths 105 to the waste storage 106, and a inlet 109 through which a reaction liquid is externally supplied into the reservoir 107 of the microchamber array 10.

As illustrated in FIG. 1B, the microchamber array 10 is made by combining transparent substrates 101, 102, and 103. The transparent substrate 101 includes the chambers 104, the first paths 105, the reservoir 107, and the inlet 109. The transparent substrate 102 includes the waste storage 106 and the second paths 108. The transparent substrates 101, 102, and 103 are, for example, resin substrates. For example, injection molding can be used to form the chambers 104, the first paths 105, the reservoir 107, the inlet 109, the waste storage 106, and the second paths 108.

The chambers 104 hold known amounts of internal standard DNA, and a primer and a fluorescent probe. The internal standard DNA has a sequence different from the sequence of the target DNA, and is amplifiable with the primer common to the target DNA to be quantified. The primer is designed to bind to the target DNA and to the internal standard DNA. The fluorescent probe is designed to bind to a part of the PCR product of the target DNA, and to a part of the PCR product of the internal standard DNA, and fluoresces differently upon binding to the PCR product of the target DNA and upon binding to the PCR product of the internal standard DNA. More specifically, the internal standard DNA, the primer, and the fluorescent probe are placed on the surfaces of the chambers 104 by applying to the surfaces of the chambers 104 followed by drying. In the microchamber array 10, the chambers 104 that belong to one group of chambers contain different amounts of internal standard DNA. That is, one group of chambers comprises a type I chamber that includes a first amount of a internal standard DNA, and a type II chamber that includes a second amount of the internal standard DNA.

As noted above, the microchamber array 10 includes the groups of chambers 201, 202, 203, 204, 205, and 206. The chambers 104 in one group of chambers contain the same internal standard DNA, the same primer, and the same fluorescent probe. A column of chambers (chambers 104 in a column) in the microchamber array 10 may contain the same amount of internal standard DNA. Here and below, in the microchamber array 10, the series of chambers 104 in a group of chambers is a row, and the series of chambers in a direction perpendicular to the rows are columns A to F.

The chambers 104 contained in a first group of chambers may include a first primer used to amplify a first target DNA, and the chambers 104 contained in a second group of chambers may contain a second primer used to amplify a second target DNA different from the first target DNA. In this way, the microchamber array 10 can be used to quantify different target DNAs.

The chambers 104 in the first group of chambers contain a first fluorescent probe that changes a fluorescence amount upon binding to the first target DNA amplified in the chambers 104 in the first group of chambers. The fluorescent probe is designed to change a fluorescence amount also upon binding to the internal standard DNA of the first target DNA. The amount of fluorescence change of the fluorescent probe is different when it binds to the first target DNA and to the internal standard DNA.

The chambers 104 in the second group of chambers contain a second fluorescent probe that changes a fluorescence amount upon binding to the second target DNA and upon binding to the internal standard DNA of the second target DNA. The second target DNA has different sequence from the sequence of the first target DNA amplified in the chambers 104 contained in the first group of chambers. In this way, the microchamber array 10 can be used to calculate regression curves of more than one target DNA.

The chambers 104 are, for example, cylindrical in shape, and have a cross sectional diameter of 500 µm, and a depth of 100 µm. The first paths 105 have a width of 200 µm and a depth of 100 µm in the cross section perpendicular to the direction of flow of the reaction mixture. The each 2 chambers 104 are spaced apart by a distance sufficient to prevent the reaction mixture from being mixed between the chambers 104.

Preferably, the inner surfaces of the chambers 104 and the first paths 105 are rendered lyophilic by a surface treatment to prevent adsorption of air bubbles. Preferably, the inner surfaces of the chambers 104 and the first paths 105 are subjected to a surface treatment that suppresses non-specific adsorption of biomolecules such as proteins.

The waste storage 106 is connected to the first paths 105 via the second paths 108. As will be described later, the waste storage 106 has a larger volume than that of the first paths 105, because the reaction mixture filling the first paths 105 discharges into the waste storage 106. The second paths 108 are formed perpendicularly through the transparent substrate 102 (for example, $\phi=90°$ in FIG. 1B).

The contact faces of the transparent substrates 101, 102, and 103 may be subjected to a liquid-repelling surface treatment, or may have a sealing property to prevent the reaction mixture from leaking out of the chambers 104 and entering other chambers 104 through the contact faces of the substrates. For example, leaking of the reaction liquid from the chambers 104 can be prevented by coating the contact faces with silicone rubber or fluororesin.

1.2. Biological Sample Quantification Method

The target DNA quantitative method according to an embodiment of the invention is a method for quantifying the target DNA contained in a biological sample using the microchamber array (biochip) 10 of the presently described embodiment. The method includes introducing a sample into each chamber 104; performing a PCR amplification in the chambers 104; measuring the fluorescence intensity of the fluorescent probe in each chamber 104, which bound to a part of the amplified DNA; determining a regression curve of the equation (1) below based on the measured fluorescence intensity in each chamber 104, and the amount of internal standard DNA used in each chamber 104; and estimating the amount of target DNA contained in the sample based on the regression curve.

$$F=a/(C+b)+c \qquad (1),$$

where F is the fluorescence intensity, C is the amount of internal standard DNA, b is the amount of target DNA contained in the sample, and a and c are predetermined values.

1.2.1. Introduction of Sample into the Chambers (Reaction Mixture Filling Method)

The following describes how a sample is introduced into the chambers 104 of the microchamber array 10. In the present embodiment, a method of filling the chambers 104 with the reaction mixture prepared from a sample is described. First, a user supplies the reaction mixture to the reservoir 107 through the inlet 109 using a pipette or the like.

The reaction mixture is prepared from a sample. For example, the reaction mixture contains the target DNA, DNA polymerase, and nucleotides (dNTPs) of concentrations suited for reaction.

The target DNA is DNA extracted from biological samples such as blood, urine, saliva, and spinal fluid, or cDNA reverse-transcribed from the extracted RNA.

Figure 2:
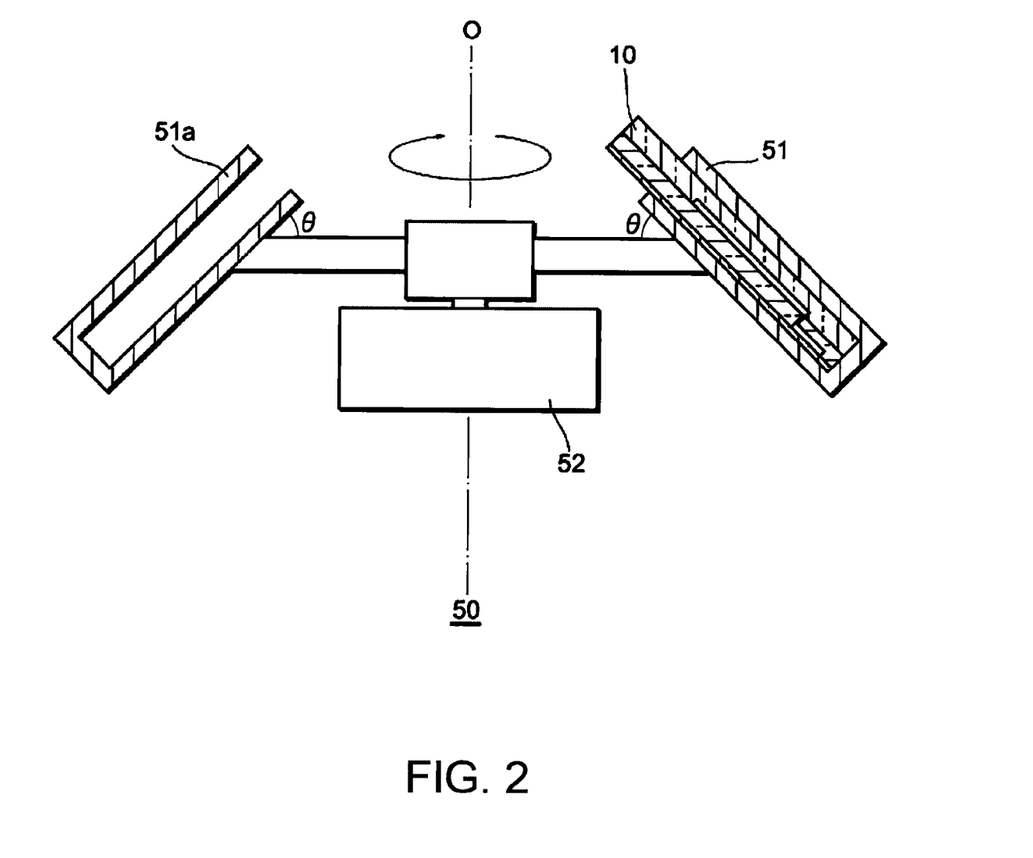
FIG. 2 is a side view of a centrifugal device in which the microchamber array according to an embodiment of the invention is installed.
Figure 3:
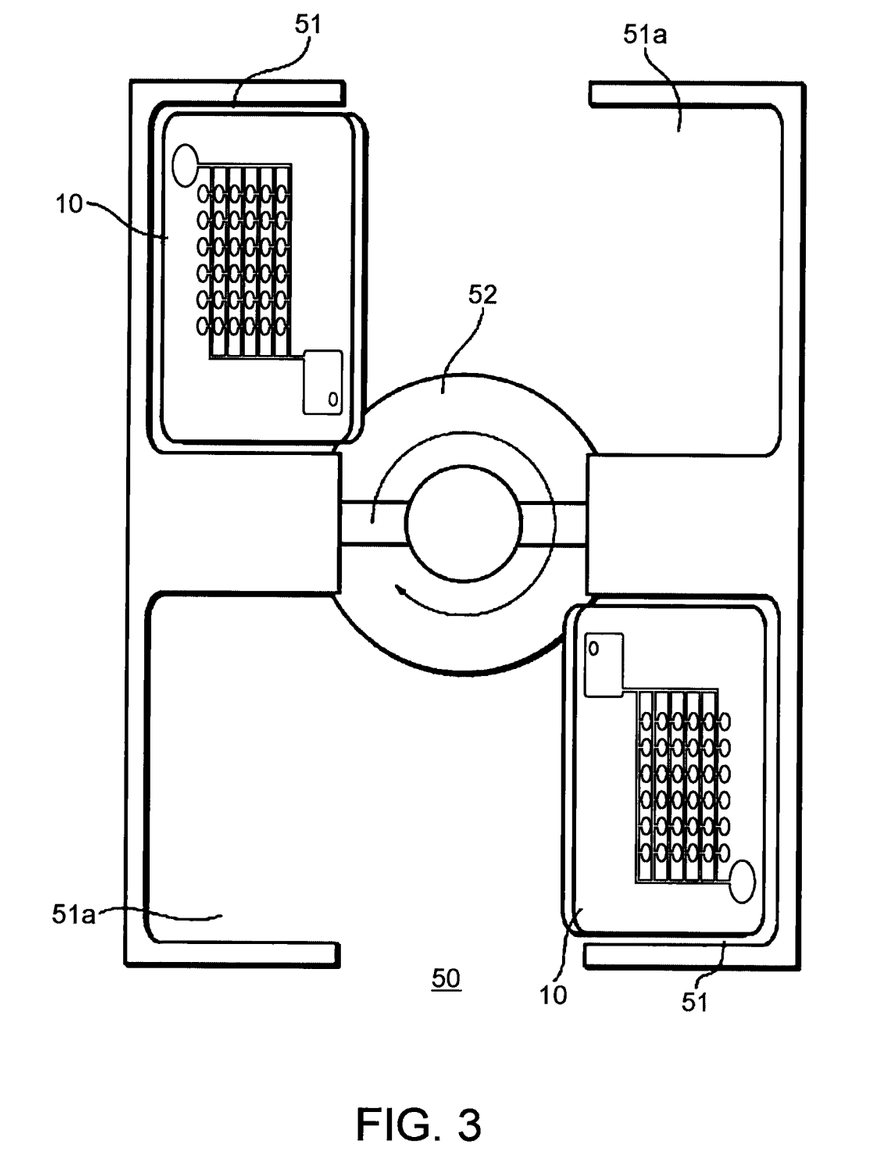
FIG. 3 is a plan view of the centrifugal device of FIG. 2 as viewed from above.

The user then rotates the microchamber array 10 with a centrifugal device 50 illustrated in FIG. 2 and FIG. 3. FIG. 2 is a side view of the centrifugal device 50. FIG. 3 is a plan view of the centrifugal device 50 as viewed from above.

As illustrated in FIG. 2 and FIG. 3, the centrifugal device 50 includes holders (rotated members) 51 attachable to the microchamber array 10, and a rotary motor (rotating member) 52. Each holder 51 is tilted with angle θ made by the microchamber array 10 with respect to the rotational axis o. Accordingly, the microchamber array 10 attached to the holder 51 is also tilted with angle θ made by the microchamber array 10 with respect to the rotational axis o. Here, θ=45°. However, the angle θ is not limited as long as it falls within the range of 0°<θ<90°.

Figure 4A:
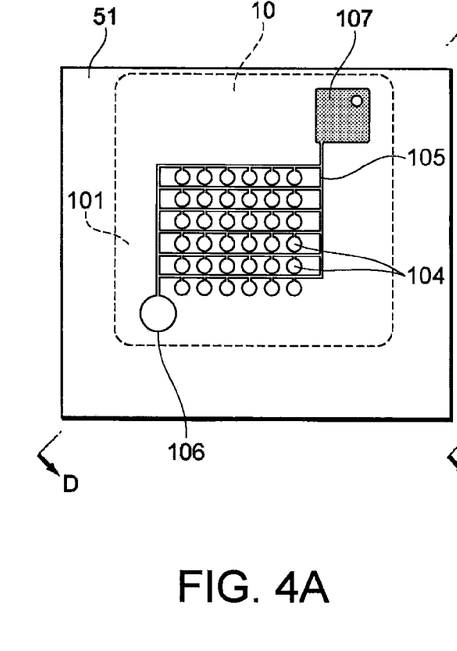
FIGS. 4A, 4B, and 4C are views illustrating the microchamber array attached to a holder of the centrifugal device of FIG. 2, as viewed from above.
Figure 4B:
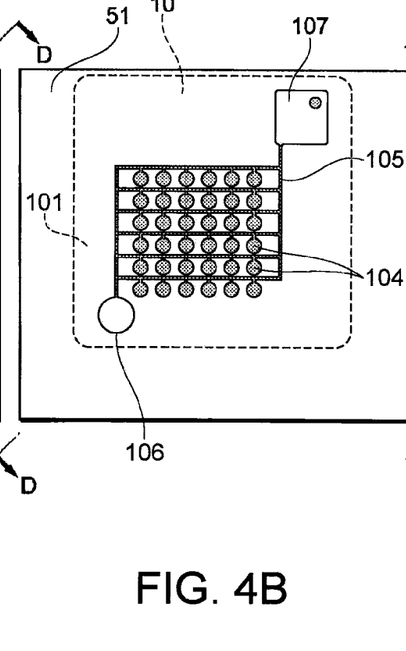
Figure 4C:
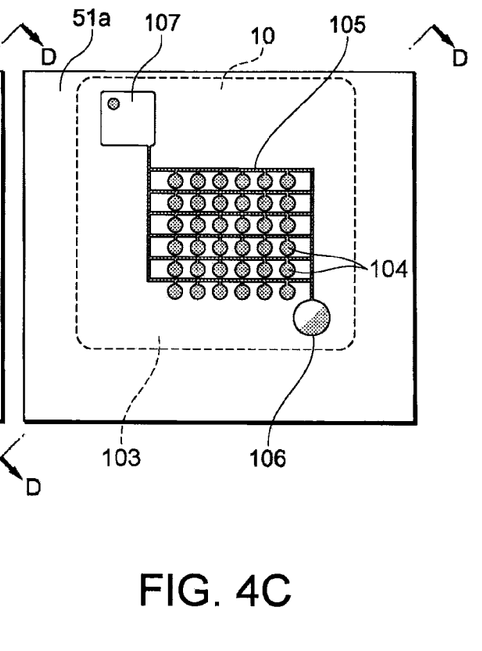
Figures 5A, 5B, 5C:
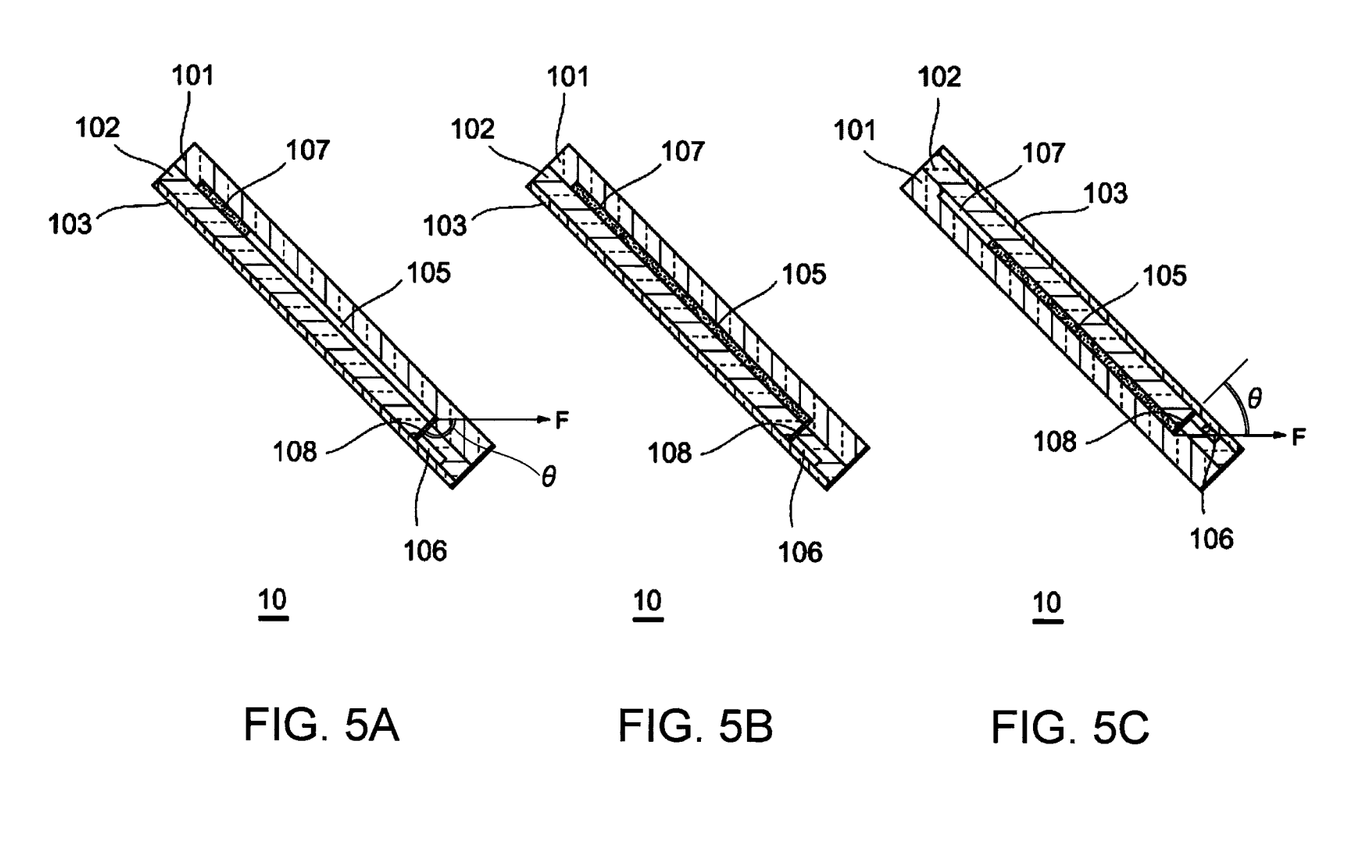
FIGS. 5A, 5B, and 5C are transverse sectional views of the microchamber array attached to the holder of the centrifugal device of FIG. 2.

FIGS. 4A, 4B, and 4C are plan views of the microchamber array 10 attached to the holder 51 of the centrifugal device 50, as viewed from above. FIGS. 5A, 5B, and 5C are transverse sectional views of the microchamber array 10 attached to the holder 51. FIGS. 5A, 5B, and 5C are D-D cross sections of FIGS. 4A, 4B, and 4C, respectively.

As illustrated in FIG. 4A and FIG. 5A, the user operates the centrifugal device 50 after setting the microchamber array 10 on the holder 51 in such a manner that the transparent substrate 101 is on the outer side with respect to the rotational axis o. The rotation exerts a centrifugal force in a direction from the reservoir 107 to the chambers 104, causing the reaction mixture in the reservoir 107 to move along the first paths 105 and fill the chambers 104. Air, having a lower specific gravity than the reaction mixture, is pushed out from chambers 104 into the first paths 105. The reaction mixture fills the chambers 104 as it replaces the air.

Here, the reaction mixture is not sent into the waste storage 106. This is because, as illustrated in FIG. 5A, the second paths 108 directed from the first paths 105 to the waste storage 106 makes a 135° angle with respect to the direction of the centrifugal force (the direction of arrow F), and thus the centrifugal force that acts in the direction from the first paths 105 to the waste storage 106 is 0 or less.

The reaction mixture is not sent into the waste storage 106 as long as the angle made by the direction of the centrifugal force and the second paths 108 directed from the first paths 105 to the waste storage 106 is 90° or more and 180° or less. Thus, when θ=45°, the reaction liquid is not sent into the waste storage 106, provided that the angle φ made by the transparent substrate 102 and the second paths 108 as in FIG. 1B falls within the range of $45° \leq \phi \leq 135°$.

As described above, because the reaction mixture does not flow towards the waste storage 106, the reaction mixture can efficiently fill all the chambers 104. After the rotation, as illustrated in FIG. 4B and FIG. 5B, all the chambers 104 and the first paths 105 are filled with the reaction mixture.

The user then stops the rotation of the centrifugal device 50, and, as illustrated in FIG. 4C and FIG. 5C, resumes the operation of the centrifugal device 50 after attaching the microchamber array 10 to the holder 51 in such a manner that the transparent substrate 103 is on the outer side with respect to the rotational axis o. The reaction mixture in the first paths 105 is sent into the waste storage 106. This is because, as illustrated in FIG. 5C, the second paths s 108 directed from the first paths 105 to the waste storage 106 makes a 45° angle with respect to the direction of the centrifugal force (the direction of arrow F), and thus the centrifugal force in the direction from the first paths 105 to the waste storage 106 is 0 or more.

The reaction mixture is sent into the waste storage 106 as long as the angle made by the direction of the centrifugal force and the second paths 108 directed from the first paths 105 to the waste storage 106 is 0° or more and less than 90°. Thus, when θ=45°, the reaction mixture is sent into the waste storage 106, provided that the angle φ made by the transparent substrate 102 and the second paths 108 as in FIG. 1B falls within the range of $45° < \phi \leq 135°$. The reaction mixture in the first paths 105 is sent into the waste storage 106, whereas the reaction mixture in the chambers 104 remains therein.

The chambers 104 are isolated from each other after the reaction mixture in the first paths 105 has been sent into the waste storage 106.

When the microchamber array 10 is set on the holder 51 for rotation in the state illustrated in FIG. 4C and FIG. 5C, the user may supply a mineral oil to the reservoir 107 through the inlet 109 using a pipette or the like. In this case, the first paths 105 are filled with the mineral oil upon rotation of the microchamber array 10. The reaction mixture in the chambers 104 is not replaced with the mineral oil because the reaction mixture has a higher specific gravity than that of the mineral oil. The isolation of each chamber 104 with the use of the oil prevents contamination between the chambers 104 (mixing of the reaction mixture in one chamber with others). Drying of the chambers 104 during the reaction process also can be prevented. A liquid having a lower specific gravity than that of the reaction liquid, and that is immiscible with the reaction mixture and does not evaporate as easily as the reaction mixture may be used instead of the mineral oil. The user may rotate the centrifugal device 50 in the state illustrated in FIG. 4C and FIG. 5C to send the reaction mixture in the first paths 105 to the waste storage 106, and may resume the rotation of the centrifugal device 50 after supplying mineral oil to the reservoir 107.

PCR (biological sample reaction) is performed after the reaction mixture has been supplied to the microchamber array 10 according to the procedures described above. Specifically, the microchamber array 10 is installed in a thermal cycler for PCR after sealing the opening of the microchamber array 10. Generally, cycling steps of dissociating double-stranded DNA at 94° C., annealing the primer at about 55° C., and replicating the complementary strands at about 72° with a heat-stable DNA polymerase are repeated.

After the PCR, the fluorescence intensity in each chamber 104 is measured with a fluorescence microscope to quantify the amount of target DNA contained in the reaction mixture in each chamber 104.

As described above, the microchamber array 10 of the present embodiment utilizes a centrifugal force to supply the reaction mixture into the chambers 104 through the first paths 105, and thus enables a reaction process for minute quantities of reaction mixture that cannot be easily quantified with the use of a pipette. Because the reaction mixture can be processed in large numbers of chambers 104 at once, different tests or procedures can be efficiently performed.

The centrifugal force is applied to first fill the first paths 105 and the chambers 104 with the reaction mixture, and reapplied in a different direction to send out the reaction mixture in the first paths 105 to the waste storage 106. In this way, contamination between the chambers 104 can be prevented, because the reaction is performed in isolation in each chamber 104. The present embodiment has been described through the use of a centrifugal force to fill the chambers 104 with the reaction mixture. However, other forces, such as the pressure of a capillary force or a pump may be used instead of a centrifugal force to fill the chambers 104.

The microchamber array 10, used as a reaction apparatus for PCR in this embodiment, also can be used for other DNA amplification reactions (for example, LAMP method).

1.2.2. Quantification of Target DNA

The target DNA quantitative method of the present embodiment further includes performing a PCR amplification in the chambers 104; measuring in each chamber 104 the fluorescence intensity of the fluorescent probe bound to a part of the amplified DNA; determining a regression curve of the equation (1) above based on the measured fluorescence intensity in each chamber 104, and the amount of internal standard DNA used in each chamber 104; and estimating the amount of target DNA contained in the sample based on the regression curve.

As described above, the chambers 104 include known amounts of internal standard DNA, and a primer and a fluorescent probe. Thus, in the PCR amplification in the chambers 104, the internal standard DNA placed in advance in the chambers 104, and the target DNA contained in the reaction mixture introduced into the chambers 104 are both amplified in the chambers 104.

The PCR amplification may be such that, for example, the fluorescent probe is designed to bind to the target DNA and to the internal standard DNA, and that the fluorescence of the fluorescent probe is quenched upon binding to the target DNA or the internal standard DNA. Fluorescence intensity in the chambers 104 is measured in this state. A regression curve of the equation (1) above is then determined based on the measured fluorescence intensities in the chambers 104, and the amount of internal standard DNA used in each chamber 104. The regression curve can then be used to estimate the amount of the target DNA contained in the sample.

The fluorescence intensity (F) in equation (1) may be (i) the fluorescence intensity of the fluorescent probe, (ii) the ratio of fluorescence intensities that is measured before the PCR amplification and after the PCR amplification, or (iii) the ratio of the fluorescence intensity measured in a heated temperature state in which the PCR product and the fluorescent probe dissociate from each other (a first state in which the fluorescent probe dissociates from the amplified DNA after the PCR amplification), and the fluorescence intensity measured at the binding temperature of the fluorescent probe (a second state in which the fluorescent probe binds to a part of the PCR product after the PCR amplification).

Assume here that the amount of fluorescence change when all the PCR products of the reaction are the PCR products of target DNA (X) is Ft, and that the amount of fluorescence change when all the PCR products are the PCR products of internal standard DNA (C) is Fc. When the chambers 104 include both the internal standard DNA and the target DNA, the PCR amplification produces the PCR products of both the internal standard DNA and the target DNA. The amount of fluorescence change F for these PCR products can be given by the following equation (2).

$$F = FtX/(X+C) + FcC/(X+C) = [X(Ft-Fc)/(X+C)] + Fc \quad (2),$$

where C is the amount of internal standard DNA in the chambers 104 (copy number), and X is the amount of target DNA in the chambers 104 (copy number).

Equation (1) can be derived from equation (2). A regression curve of equation (1) can be obtained by plotting the amount of fluorescence change (F) of each chamber 104 on the vertical axis against the amount of internal standard DNA (log C) contained in each chambers 104 of the same group of chambers on the horizontal axis (see, for example, FIG. 9 described later). The value of b in the three parameters a, b, and c in equation (1) determined from the regression curve corresponds to the amount of the target DNA.

Any fluorescent probe can be used as long as it can bind to a part of the PCR product of the target DNA, and shows different fluorescence changes for the target DNA and the internal standard DNA. Examples of such fluorescent probes include Taqman Probe®, Hyb Probe®, Molecular Beacon®, and Q-Probe®. Q-Probe is a probe used to detect target DNAs by utilizing the "fluorescence quenching phenomenon", in which the intensity of emitted fluorescence decreases as a guanine base approaches a labeled fluorescent dye.

Q-Probe is designed to have a sequence that has a fluorescent-labeled cytosine at one terminal, and that specifically binds to the target DNA. Upon binding of the Q-Probe to the target DNA, fluorescence intensity decreases under the influence of a guanine. When the target DNA quantitative method of the present embodiment is to use a competitive PCR method with a Q-Probe, the base of the target DNA corresponding to the fluorescent-labeled terminal base of the Q-probe cannot be a guanine when a guanine is the corresponding base of the internal standard DNA for the fluorescent-labeled terminal base of the Q-Probe. As long as this is the case in the coamplification of the target DNA and the internal standard DNA using a Q-probe, the fluorescence intensity of the labeled fluorescent dye decreases (quenches) upon hybridization of the internal standard DNA with the Q-Probe, whereas the fluorescence intensity of the labeled fluorescent dye does not decrease upon hybridization of the target DNA with the Q-Probe. Here, the target DNA and the internal standard DNA can be read the other way around. That is, whether to cause quenching of the fluorescence upon binding of the Q-Probe to the target DNA or the internal standard DNA is arbitrary.

The target DNA quantitative method of the present embodiment can be used to quantify multiple test items from a sample, using the groups of chambers of the microchamber array 10. For example, the method can be used for the gene testing of food poisoning-causing microorganisms (specifically, for the testing of pathogenic microorganisms in food, or the testing of pathogenic microorganisms in a sample (feces) collected from patients suffering from food poisoning).

In this case, genes of the pathogenic microorganisms are used as the target DNAs in the chambers 104 of the groups of chambers, and the internal standard DNAs set for these target DNAs are placed in these groups of chambers. Genes of different causative microorganisms can be quantified in each group of chambers. Examples of food poisoning-causing microorganisms include campylobacters, salmonellas, *Pseudomonas aeruginosa*, pathogenic *Escherichia coli* O-157, and *Staphylococcus aureus*. Fluorescent probes (for example, Q-probe) designed to hybridize with the target DNAs and the internal standard DNAs are then placed in the chambers 104 of each group of chambers, and the target DNAs are quantified using the quantitative method described above. In this way, multiple items of target DNA quantification can be performed with ease from a single sample.

2. Examples

The following describes the present invention in more detail based on an example. It should be noted, however, that the invention is not limited to the following.

This example describes a quantification method of the target DNA in a sample using PCR with the microchamber array 10 of FIGS. 1A and 1B, using a Q-Probe (Kurata et al., Nucleic acids Research, 2001, vol. 29, No. 6 e34) as the fluorescent probe.

The fluorescence of the Q-Probe is quenched by the interaction with the guanine contained in the nucleic acid to which the Q-probe binds. When the Q-probe is that which can bind to both the target DNA and the internal standard DNA, and has fluorescence quenched upon binding to one of the target DNA and the internal standard DNA, a relative amount of the target DNA with respect to known amounts of internal standard DNA can be estimated.

The inventor purchased the target DNA and the internal standard DNA from J-Bio21 Corporation. The inventor used a mixture of 10 mM Tris-HCl buffer (pH: 8.3), 50 mM KCl, and 1.5 mM MgCl$_2$.

Figure 6:
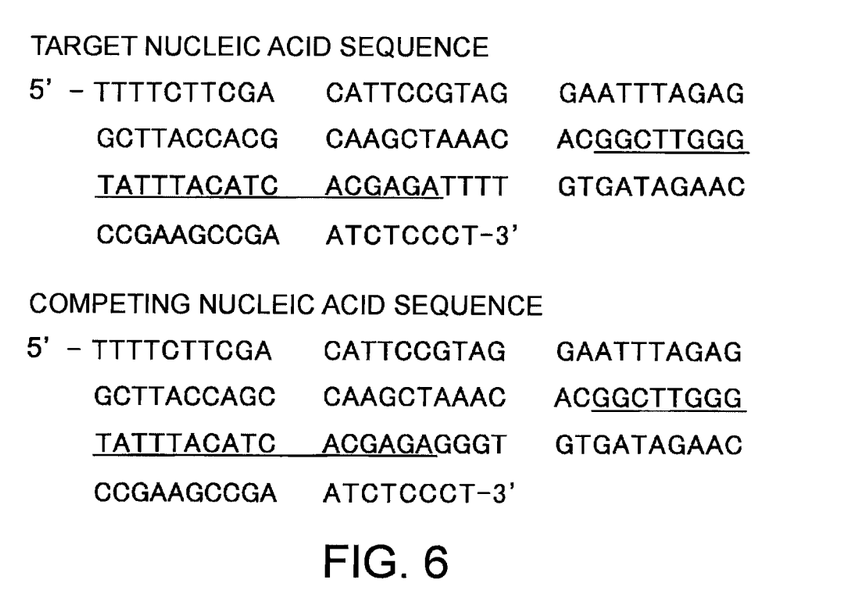
FIG. 6 is a view showing examples of the sequences of a target DNA and a internal standard DNA used in Example 1 of the invention.

FIG. 6 represents examples of target DNA and internal standard DNA sequences. The Q-probe binds to the underlined portions. As shown in FIG. 6, the target DNA has the sequence TTTT, and the internal standard DNA the sequence GGGT immediately after the binding sites (underlined portions) for the fluorescent probe. Thus, the fluorescence of the Q-Probe is quenched by the reaction with the guanine (G) at the binding site upon binding to the internal standard DNA.

Figure 7:
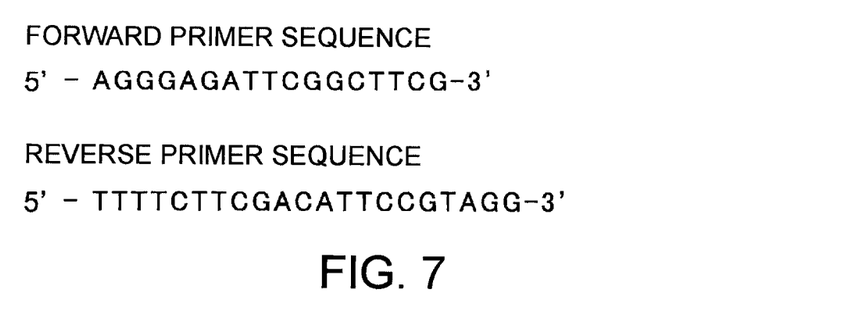
FIG. 7 is a view showing an example of the sequences of primers used in Example 1 of the invention.
Figure 8:
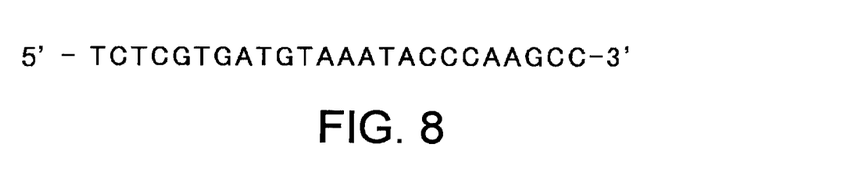
FIG. 8 is a view showing a sequence of a Q-probe used in Example 1 of the invention.

The inventor placed the primers and the fluorescent probe by applying on the surfaces of the chambers 104 of the microchamber array 10 of FIGS. 1A and 1B followed by vacuum drying. The primers have the sequences shown in FIG. 7. The fluorescent probe (Q-Probe) has the sequence shown in FIG. 8. The Q-Probe was fluorescent-labeled using a BODIPY FL (Molecular probes).

Known amounts of internal standard DNA were applied and vacuum dried on the surfaces of the chambers 104 in different amounts for the chamber columns A to F. Table 1 shows the amounts (copy numbers) of internal standard DNA placed in the chambers 104 of the chamber columns A to F.

TABLE 1

| Chamber column | Internal standard DNA |
|---|---|
| A | 100 copies |
| B | 1,000 copies |
| C | 10,000 copies |
| D | 100,000 copies |
| E | 1,000,000 copies |
| F | — |

The inventor then charged a target DNA-containing reaction liquid into the chambers 104, and conducted PCR using a thermal cycler (Master Cycler®, Eppendorf; a LightCycler 480®, Roche Diagnostics). The reaction mixture contained a LightCycler 480® Genotyping Master, and a uracil DNA glycosylase (both purchased from Roche Diagnostics). Quantification accuracy was ascertained by using four samples 1 to 4 with different amounts (copy numbers) of target DNA in four microchamber arrays 10 (Table 2). Fluorescence measurements were made at room temperature before the amplification reaction, and at room temperature, 60° C., and 95° C. after the amplification reaction.

TABLE 2

| Sample | Target DNA |
|---|---|
| 1 | 100 copies |
| 2 | 1,000 copies |
| 3 | 10,000 copies |
| 4 | 100,000 copies |

Figure 9:
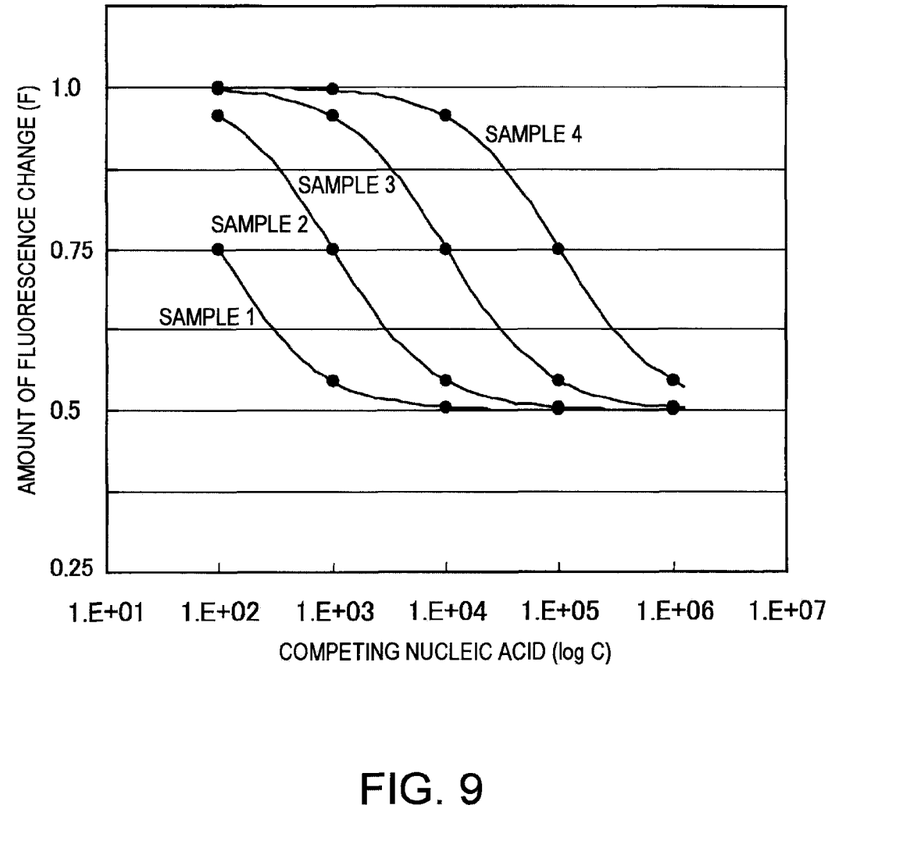
FIG. 9 is a diagram representing the relationship (regression curve) between the amount of internal standard DNA (log C) and fluorescence intensity (amount of change) F in the samples quantified in Example 1 of the invention.

The chamber columns A to F contained different amounts of internal standard DNA. FIG. 9 is a graph representing the amount of fluorescence change (F) of each chamber 104 plotted on the vertical axis against the amount of internal standard DNA (log C) on the horizontal axis for samples 1 to 4. Regression curves of samples 1 to 4 were obtained from the graph. Then, the parameters a, b, and c in equation (1) were found from the regression curves. The value of b corresponds to the amount of the target DNA. From FIG. 9 and equation (1), the values of b (amounts of target DNA) for samples 1 to 4 were calculated as 40, 850, 9,210, and 89,700 copies, respectively.

This example shows the quantification result for only one kind of target DNA. However, the microchamber array 10 can be used for the quantification of different target DNAs by introducing different target DNAs and reagents (primers, fluorescent probes) for the amplification and quantification of these target DNAs to each group of chambers.

As described above, the microchamber array 10 in this example is used to conduct nucleic acid amplification reaction (PCR) using different amounts of internal standard DNA in the chambers 104 of one group of chambers. The fluorescence intensity in each chamber 104 can be obtained by measuring the fluorescence intensity of the fluorescent probe that has bound to a part of the PCR amplified DNA. A regression curve of equation (1) expressed as the relationship between the amount of fluorescence change (F) and the amount of internal standard DNA (log C) in the sample is obtained based on the measured fluorescence intensity and the amounts of internal standard DNA used in the chambers 104. The regression curve can then be used to estimate the amount of target DNA in the sample. Quantitative analysis of the target DNA can be performed in this manner both accurately and efficiently.

The present invention encompasses configurations essentially the same as those described in the embodiment (for example, a configuration with the same functions, methods, and results, and a configuration with the same object and results). The invention also encompasses configurations that have replaced non-essential components of the configurations described in the embodiment. The invention also encompasses configurations that have the same effects or achieve the same object as the configurations described in the embodiment. The invention also encompasses configurations that include the configurations of the foregoing embodiment in combination with the related art.

What is claimed is:
1. A biochip, comprising:
a supply reservoir:
a waste chamber:
a first group of chambers, each chamber of the first group of chambers including:
   a type I chamber including:
      a primer that is designed to bind to the target DNA;
      an internal standard DNA of a first amount that has a sequence different from a sequence of the target DNA, and is amplifiable with the primer; and
      a fluorescent probe that is designed to bind to a part of a PCR product of the target DNA and to a part of a PCR product of the internal standard DNA, and fluoresces differently for the PCR product of the target DNA and the PCR product of the internal standard DNA, and
   a type II chamber including;
      the internal standard DNA of a second amount different from the first amount;
      the primer; and
      the fluorescent probe,
wherein the supply reservoir, the waste chamber, and each of the type I and type II chambers are formed between a first substrate and a second substrate, and
the supply reservoir, each of the type I chambers and the type II chambers, and the waste chamber define a plurality of pathways formed between the first substrate and the second substrate; and
wherein the plurality of pathways are configured such that in a first orientation the plurality of pathways prevent a reaction mixture of the primers, the fluorescent probes, and the internal standard DNAs from flowing to the waste chamber, and in a second orientation the plurality of pathways allow the reaction mixture to flow to the waste chamber.

2. The biochip according to claim 1,
wherein the plurality of pathways include a first path connected to the type I chamber and the type II chamber; and
the supply reservoir is connected to the first path.

3. A biochip, comprising:
a supply reservoir:
a waste chamber:
a first group of chambers, each chamber of the first group of chambers including:
   a first type I chamber including:
      a first primer that is designed to bind to the target DNA;
      a first internal standard DNA of a first amount that has a sequence different from a sequence of the target DNA, and is amplifiable with the first primer; and
      a first fluorescent probe that is designed to bind to a part of a PCR product of the target DNA and to a part of a PCR product of the first internal standard DNA, and fluoresces differently for the PCR product of the target DNA and the PCR product of the first internal standard DNA, and
   a first type II chamber including:
      the internal standard DNA of a second amount different from the first amount;
      the first primer; and
      the first fluorescent probe, wherein the supply reservoir, the waste chamber, and each of the first type I and first type II chambers are formed between a first substrate and a second substrate, and the supply reservoir, each of the first type I chambers, the first type II chambers, and the waste chamber are connected by a plurality of pathways formed between the first substrate and the second substrate; and a second group of chambers, each chamber of the second group of chambers including:

a second type I chamber including:
- a second primer different from the first primer that is designed to bind to the target DNA;
- a second internal standard DNA different from the first internal standard DNA of a third amount that has a sequence different from a sequence of the target DNA, and is amplifiable with the second primer; and
- a second fluorescent probe that is designed to bind to a part of a PCR product of the target DNA and to a part of a PCR product of the second internal standard DNA, and fluoresces differently for the PCR product of the target DNA and the PCR product of the second internal standard DNA, and a second type II chamber including:
- the second internal standard DNA of a fourth amount different from the third amount;
- the second primer; and
- the second fluorescent probe, wherein each of the second type I and second type II chambers are formed between the first substrate and the second substrate, and the supply reservoir, each of the second type I chambers, the second type II chambers, and the waste chamber are connected by another plurality of pathways formed between the first substrate and the second substrate, wherein the plurality of pathways and the another plurality of pathways are each configured such that the plurality of pathways and the another plurality of pathways in a first orientation prevent a reaction mixture of the primers, the fluorescent probes, and the internal standard DNAs from flowing to the waste chamber, and in a second orientation the plurality of pathways and the another plurality of pathways allow the reaction mixture to flow to the waste chamber.

* * * * *

SEQUENCE LISTING

```
<160> NUMBER OF SEQ ID NOS: 5

<210> SEQ ID NO 1
<211> LENGTH: 108
<212> TYPE: DNA
<213> ORGANISM: Artificial Sequence
<220> FEATURE:
<223> OTHER INFORMATION: Target nucleic acid

<400> SEQUENCE: 1
ttttcttcga cattccgtag gaatttagag gcttaccacg caagctaaac acggcttggg      60
tatttacatc acgagatttt gtgatagaac ccgaagccga atctccct                  108

<210> SEQ ID NO 2
<211> LENGTH: 108
<212> TYPE: DNA
<213> ORGANISM: Artificial Sequence
<220> FEATURE:
<223> OTHER INFORMATION: Competitive nucleic acid

<400> SEQUENCE: 2
```

-continued

```
ttttcttcga cattccgtag gaatttagag gcttaccagc caagctaaac acggcttggg    60
tatttacatc acgagagggt gtgatagaac ccgaagccga atctccct                108
```

<210> SEQ ID NO 3
<211> LENGTH: 17
<212> TYPE: DNA
<213> ORGANISM: Artificial Sequence
<220> FEATURE:
<223> OTHER INFORMATION: Forward primer sequence

<400> SEQUENCE: 3

```
agggagattc ggcttcg                                                   17
```

<210> SEQ ID NO 4
<211> LENGTH: 21
<212> TYPE: DNA
<213> ORGANISM: Artificial Sequence
<220> FEATURE:
<223> OTHER INFORMATION: Reverse primer sequence

<400> SEQUENCE: 4

```
ttttcttcga cattccgtag g                                              21
```

<210> SEQ ID NO 5
<211> LENGTH: 24
<212> TYPE: DNA
<213> ORGANISM: Artificial Sequence
<220> FEATURE:
<223> OTHER INFORMATION: sequence of Q-probe

<400> SEQUENCE: 5

```
tctcgtgatg taaataccca agcc                                           24
```